United States Patent
Myllymäki et al.

(10) Patent No.: US 11,482,333 B2
(45) Date of Patent: Oct. 25, 2022

(54) METHOD AND AN APPARATUS FOR DETERMINING INJURY RISK OF A PERSON BASED ON PHYSIOLOGICAL DATA

(71) Applicant: Firstbeat Analytics Oy, Jyväskylä (FI)

(72) Inventors: Tero Myllymäki, Jyväskylä (FI); Joonas Korhonen, Jyväskylä (FI); Tuukka Ruhanen, Jyväskylä (FI); Mikko Seppänen, Jyväskylä (FI); Veli-Pekka Kurunmäki, Jyväskylä (FI)

(73) Assignee: Firstbeat Analytics Oy

( * ) Notice: Subject to any disclaimer, the term of this patent is extended or adjusted under 35 U.S.C. 154(b) by 962 days.

(21) Appl. No.: 16/242,197

(22) Filed: Jan. 8, 2019

(65) Prior Publication Data
US 2019/0214144 A1    Jul. 11, 2019

(30) Foreign Application Priority Data
Jan. 8, 2018 (FI) .................................. 20185018

(51) Int. Cl.
*G16H 50/30*  (2018.01)
*A61B 5/024*  (2006.01)
(Continued)

(52) U.S. Cl.
CPC ......... *G16H 50/30* (2018.01); *A61B 5/02405* (2013.01); *A61B 5/02438* (2013.01); *A61B 5/7275* (2013.01); *G16H 20/30* (2018.01)

(58) Field of Classification Search
CPC .... G16H 50/30; G16H 20/30; A61B 5/02405; A61B 5/02438; A61B 5/7275
See application file for complete search history.

(56) References Cited

U.S. PATENT DOCUMENTS 7,192,401 B2 * 3/2007 Saalasti ................. A61B 5/222
                                                  600/509
9,162,108 B1 * 10/2015 Launis ............... A63B 21/0628
(Continued)

FOREIGN PATENT DOCUMENTS

EP    1897598 A1    3/2008
EP    3340248 A1    6/2018

OTHER PUBLICATIONS

Search Report dated Jul. 18, 2018 in corresponding Finnish Application No. 20185018; 2 pages.
(Continued)

*Primary Examiner* — Mohamed Charioui
*Assistant Examiner* — Christine Y Liao
(74) *Attorney, Agent, or Firm* — Samuel M. Korte; Max M. Ali

(57) ABSTRACT

An apparatus and method for determining injury risk from plurality of exercises using a device with a heart rate sensor, a processor, memory including a resident memory, an output device and software. For example the method may: determine and store values of Training load of each exercise in the resident memory obtaining a register, perform a HRV-based Recovery Test and storing Recovery values in the register, calculate indices depicting Short Term Training Load, ratio of Short Term Training Load to Long Term Training Load, and Recovery, calculate weighting factors for each said index, correct each index with corresponding weighting factor to obtain weighted indices, calculate a value of the Injury Risk using the weighted indices, and display the value of Injury Risk.

12 Claims, 8 Drawing Sheets

(51) Int. Cl.
 *A61B 5/00* (2006.01)
 *G16H 20/30* (2018.01)

(56) References Cited

U.S. PATENT DOCUMENTS

| | | |
|---|---|---|
| 2003/0050537 A1 | 3/2003 | Wessel |
| 2008/0146334 A1 | 6/2008 | Kil |
| 2009/0006130 A1* | 1/2009 | Taylor .................... G06Q 10/10 705/2 |
| 2010/0076278 A1 | 3/2010 | van der Zande et al. |
| 2010/0312076 A1 | 12/2010 | Bly et al. |
| 2014/0288449 A1 | 9/2014 | Wegerif |
| 2017/0080346 A1 | 3/2017 | Abbas |
| 2018/0174685 A1 | 6/2018 | Hamalainen et al. |
| 2018/0310874 A1 | 11/2018 | Myllymaki et al. |

OTHER PUBLICATIONS

Search Report dated Apr. 24, 2019 in corresponding European Application No. 19150719; 2 pages.

* cited by examiner

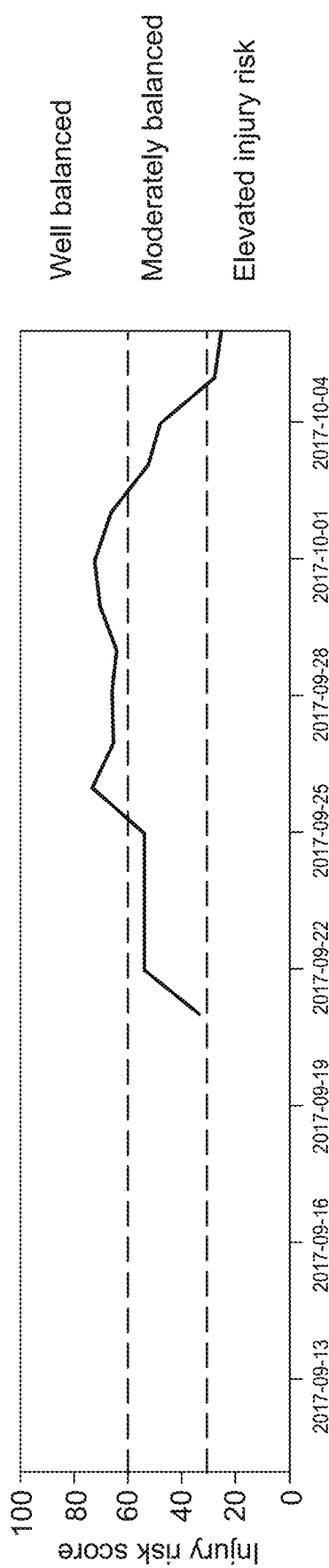
FIG. 5a
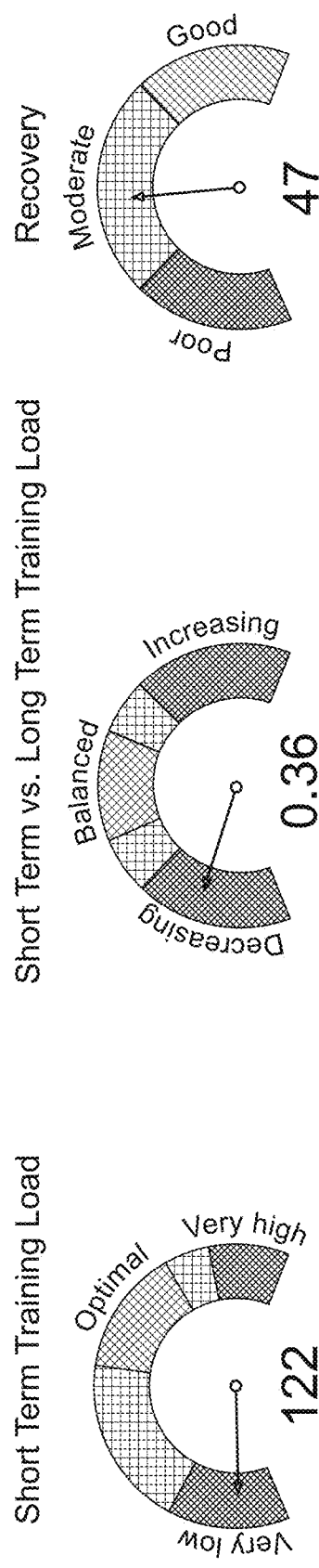
FIG. 5b
FIG. 5c
FIG. 5d

Team player status analysis

Teams overall training status: 61.1 Balanced

● Not available: 0   ◉ Elevated injury risk: 1   ◍ Moderately balanced: 3   ○ Balanced: 7

| | | | | |
|---|---|---|---|---|
| Athlete3 | 16 | Athlete6 | 34 | Athlete9 | 62 |
| | | Athlete4 | 42 | Athlete11 | 65 |
| | | Athlete8 | 47 | Athlete2 | 69 |
| | | | | Athlete1 | 75 |
| | | | | Athlete5 | 81 |
| | | | | Athlete10 | 87 |
| | | | | Athlete7 | 93 |

FIG. 6

METHOD AND AN APPARATUS FOR DETERMINING INJURY RISK OF A PERSON BASED ON PHYSIOLOGICAL DATA

FIELD

The invention is related to a method for determining injury risk of a user from plurality of exercises using a device with a heart rate sensor, a processor, memory having a resident memory, an output device and software, the injury risk being determined using value depicting Short Term Training Load (STTL-value) and Long Training Term Load (LTTL-value), the method has following steps implemented with said device:
- determining in each physical exercise a timestamp and a value of Training load,
- storing the timestamp and the value of Training load of each exercise in the resident memory obtaining a register having plurality of such records from executed exercises,
- performing a HRV-based Recovery Test frequently obtaining a Recovery value with a time stamp from each Recovery Test and storing said Recovery values with the time stamp in the register of the resident memory.

The invention is also related to an apparatus for determining injury risk.

BACKGROUND

Sporting activity, especially at professional level, always includes a risk for soft-tissue, overuse injuries due to load on the athlete's body caused by training and competing. The central aspect of improving performance capabilities is to challenge the body's physiological homeostasis and by this way elicit physiological adaptations. The "training load" may be a measure of how much physical work has been performed through activity with respect to the duration of exercise. In other words, the training load may be a measure of how much body's homeostasis has been disturbed by physical activity.

Different intensities and durations of exercise sessions creates a cumulative training load which can be viewed in short-term (acute) but also in longer-term (chronic), the latter expressing a load an athlete is typically accustomed to tolerate.

One of the most important aspects of effective training is to control the training load, i.e. how much homeostasis has been disturbed by training, and how this load on the body is changing over time. In addition to calculation of training load, the disturbance of the body's homeostasis can also be monitored through analysis of recovery from training, for example, through analysis of autonomic nervous system activity via heart rate variability (HRV). Poor recovery is associated with, for example, muscular strain and fatigue, decreased coordination skills, and worsened efficiency and economy of body movements, all increasing the overall risk for overuse injuries. Monitoring training load and recovery is vital to ensure that athletes train at an optimal level towards their goals and avoid overloading. Appropriate load and recovery monitoring aids in determining whether an athlete is adapting to a training program and is minimizing the risk of overtraining, developing illness, and/or injury.

To be able to make decisions on future training and competing a user needs to know how balanced their training has been and at what level their injury risk is. It is important also for coaches to know whether their athletes are able to tolerate the prescribed training and adjust the load if needed. For optimally balanced training, one should try to avoid very quick changes in training load relative to what an athlete has accustomed to. In addition, it is important to ensure the athlete is able to recover from the training load. This requires not only information on each individual exercise, but information on a plurality of exercises to determine the cumulative effect they have had on a user's injury risk.

Heart rate monitoring based injury risk assessment using physiological data from multiple exercises is not currently available. At first sight that kind of application seems to need a lot of resources. Another challenge requiring solving is how to evaluate injury risk from plurality of parameters taken at different time points which are many times changing, i.e. not all the parameters are available at each time point. Embedded systems, such as heart rate monitors, fitness devices, mobile phones, PDA devices, tablet computers, or wrist top computers have quite limited CPU and memory resources to be used by any utility application. Those resources are only a fraction of that of an ordinary PC. This is a challenge for an implementation of any physiological method.

The applicant's own prior patent application EP 3340248 A1 discloses a method for determining a training status for a user. The training status is a current trajectory of the user's training. In the method information is measured from each individual exercise as well as on a plurality of individual exercises to determine the cumulative effect they have had on a user's fitness. However, it is hard for the user to conclude the level of injury risk just based on the training status.

The purpose of the invention is to achieve an automated method and apparatus for assessment of risk of injury which requires very limited amount of hardware resources as well as resources of the user. By resources of the user it is meant that the method requires very little time from the user, just a couple of minutes per day in addition to those exercises that have been done.

SUMMARY

The current invention is directed towards a method and apparatus to determine injury risk of a person from a plurality of exercises, where the method can be implemented in an embedded device having limited CPU and memory resources and having a host system.

The purpose of the invention can be achieved by a method for determining injury risk of a user from plurality of exercises using a device with a heart rate sensor, a processor, memory having a resident memory, an output device and software, the injury risk being determined using value depicting Short Term Training Load and Long Training Term Load. The method has following steps implemented with said device, the steps being determining in each physical exercise a timestamp and a value of Training load, storing the timestamp and the value of Training load of each exercise in the resident memory obtaining a register having plurality of such records from executed exercises, as well as performing a HRV-based Recovery Test frequently obtaining Recovery values with a time stamp and storing said Recovery values in the register. The method further includes steps of calculating indices depicting Short Term Training Load (STTL), ratio of Short Term Training Load (STTL) and Long Term Training Load (LTTL), and Recovery (RI) based on the values stored on the register of the resident memory, and calculating weighting factors for each said index, each weighting factor depicting the relevance of corresponding index to the probability of injury. In addition the method includes steps of correcting each index with corresponding weighting factor to obtain weighted indices, calculating a numerical value of Injury Risk using the weighted indices and displaying the value of Injury Risk to user using the output device.

Using the method according to the invention the characteristics of exercises as well as recovery test or tests can be used to calculate a value for the risk of injury to occur in a very simple and quick manner. The method automatically converts different data into a very simple value of injury risk, which is for the user to understand. The use of indices of Short and Long Term Training Load and Recovery values enables indices to be compared in order to assess the injury risk using numerical values. Weighting factors are used to take into account the importance of each index in the calculation.

In this context term "Recovery Test" must be understood so that it may include calculation of recovery and the third index that are initiated either automatically or manually by the user. "Recovery Test" may be a user initiated test that is performed when the user desires or it may be an automated sequence performed by the software automatically at chosen intervals. It must also be understood that recovery test may be performed at any time, for example, after an exercise, but also during an exercise or even during sleep. HRV-calculation of the recovery test is executed preferably on a predetermined period.

Preferably indices are calculated using scaling functions which are namely first scaling function for calculating a first index depicting Short Term Training Load (STTL), second scaling function for calculating a second index depicting ratio of Short Term Training Load (STTL) and Long Term Training Load (LTTL) and third scaling function for calculating a third index depicting Recovery. By using scaling functions the different characteristics of exercises and recovery test can be transformed into values enabling calculation of injury risk.

Preferably correcting of each index with said weighting factor is done by multiplying each index with corresponding weighting factor.

Displayed value of the injury risk may be displayed also in graphical form instead of a numerical value.

Recovery test is performed frequently, more precisely preferably 1-7 times per week. Frequently performed recovery tests ensure that an adequate amount of data is there to be used for reliable injury risk calculation.

According to an embodiment if the highest value of the injury risk depicts lowest possible probability of injury, the first scaling function is such that the value of the first index increases to a maximum as the value of Short Term Training Load increases up to a predetermined value and the value of the first index decreases as the value of Short Term Training Load increases higher than the predetermined value, the second scaling function is such that value of second index reduces when the value of ratio of Short Term Training Load (STTL) to Long Term Training Load (LTTL) differs from 1 and the third scaling function is such that the value of the third index increases when the Recovery Test result increases until a threshold value of Recovery test has been reached. In this embodiment the value of injury risk is high when the risk of injury is low. By using separate scaling functions each aspect of injury risk calculation, i.e. STTL, ratio of STTL to LTTL and Recovery can be scaled into value range, such as 0-100.

Alternatively if the lowest value of injury risk depicts lowest possible probability of injury, then the first scaling function is such that the value of the first index decreases to minimum as the value of Short Term Training Load increases up to a predetermined value and the value of the first index increases as the value of Short Term Training Load increases higher than the predetermined value, the second scaling function is such that the value of the second index increases when the value of ratio of Short Term Training Load (STTL) to Long Term Training Load (LTTL) differs from 1 and the third scaling function is such that the value of the third index decreases when the Recovery Test result decreases until a threshold value of Recovery test has been reached.

Preferably the recovery test is a Quick Recovery test (QRT), the duration of which can be 1-10 minutes, preferably 2-4 minutes. This means that the information related to recovery which is needed to assess the injury risk in addition to exercise data can be derived from the Quick Recovery Test quickly without spending too much time or effort. This encourages the user to do Quick Recovery Tests quite often which in turn improves the reliability of the method.

The steps of Quick Recovery test may include steps of measuring beat-by-beat HR for 3 min, using QRT formula to get an absolute QR value from HRV and HR and scaling the values with personal QRT history using the average and standard deviation of the result for scaling. This kind of recovery test requires only very little time from the user and is easy to do.

The QRT formula is such that the recovery value is a maximum of heart rate variability-to-heart rate ratio averages, where the averages are calculated from a predetermined length period (e.g. 1 minute) over the whole measurement.

The scaling of recovery value is done by using a linear function limited to interval [0, 100], where 0 and 100 limits are values based on personal QRT (Quick Recovery test value) mean and personal QRT standard deviation. The 0 limit can be 1.2-1.5, preferably 1.3-1.4 times the personal QRT standard deviation subtracted from the personal QRT mean, and similarly the 100 limit can be 1.8-2.2, preferably 1.9-2.1 times the personal QRT standard deviation added to the personal QRT mean.

Values of the indices are preferably scaled in a predetermined range, e.g. in a scale 0-100. By scaling the values, the indices can be used in the calculation of the value of injury risk.

According to an embodiment the weighting factors are first weighting factor, second weighting factor and third weighting factor, wherein the first weighting factor is calculated using a first weighting function depicting reliability of the first index, the second weighting factor is calculated using a second weighting function depicting reliability of the second index and the third weighting factor is calculated using a third weighting function depicting reliability of the third index. By using weighted indices the real effect of each index can be taken into account in the calculation of injury risk. For example, if data of recovery includes only one Recovery value that is 8 days old, the second index depicting the Recovery value and Recovery value is given a relative low weight in the calculation. On the other hand, if there is three Recovery values from the last three days, the weight of Recovery value is given a higher weight.

The third weighting function can be an average of values of a fourth weighting function, which is a function of timing of the QRT, and a fifth weighting function which is a function of average result of the QRT test. This kind of calculation involving fourth and fifth weighting function increases the reliability of calculation since both timing and trend of recovery affect the weighting of recovery in the calculation of injury risk.

Preferably the third weighting factor is calculated by calculating a sub-factor for each Recovery value using said fourth weighting function and fifth weighting function and by calculating an average of the sub-factors, the average being the third weighting factor. By using sub-factors both timing and score of the recovery test can be considered when assessing the effect of recovery to the value of injury risk.

The third index is may be calculated by obtaining at least two, preferably three latest Recovery values, scaling the Recovery values using third scaling function, calculating a second average of the scaled Recovery values, the second average being the third index. By using two or more recovery test for calculation of the third index the reliability of the injury risk calculation improves when recovery over a longer period of time is known.

According to an embodiment calculation of Injury risk includes the steps of scaling the values of indices stored in the register to form scaled indices wherein, scaled value of the first index has a peak value before STTL is 100% from personal maximum value, scaled value of the second index has a peak value when ratio is invariable and scaled value of the third index increases with improved recovery value until a peak value is reached. This kind of scaling enables the use of indices in automated injury risk assessment when relevance of training and recovery can be converted to numerical value. The embodiment above describes the injury risk with the injury risk value that derives its highest value when the injury risk is lowest. Naturally the method can also be implemented in opposite manner, wherein the injury risk is the highest when the injury risk value is the highest. In that kind of implementation the indices derive their peak differently.

According to an embodiment the calculation of injury risk steps of multiplying the scaled indices each with a corresponding weighting factor that is calculated using a weighting function, in which the first weighting function is constant, the second weighting function increases the value of the second weighting factor as the number of exercises per week increases, and the third weighting function giving a peak value for the third weighting factor at lowest recovery value. With weighting factor the relevance of each index can be considered in the automated calculation of injury risk. This means that the method requires no additional input from the user when exercises and QRT are measured.

Preferably the value of injury risk is calculated using following equation IR=(STTL+w_Ratio*Ratio+w_QRI*QRI)/(1+w_Ratio+w_QRI), wherein STTL is scaled value of the first index, w_Ratio is the second weighting function of the second indices, Ratio is scaled value of the second index, w_QRI is the third weighting function of the third index and QRI is scaled value of the third index. The calculation of the value of injury risk using the above equation is simple and quick.

According to an embodiment the method includes steps of determining Training Load of each exercise using a basic library (ETE) for monitoring the exercises and determining characteristics of the plurality of exercises in a host process using a dynamic memory, the characteristics being preferably at least the timestamp and a value of Training load, determining Recovery value of each Recovery Test using a basic library (ETE) for determining characteristics of the Recovery Test in a host process using a dynamic memory, the characteristics being preferably at least the timestamp and a score of Recovery Test, storing the exercise characteristics in a resident memory and determining the value of injury risk using an auxiliary library software (STHA) as a child process using the characteristics in the resident memory. By using ETE and STHA libraries in the calculation the amount of data stored in the resident memory is reduced and therefore less capacity is required.

Preferably the first index and the second index are calculated based on the values of Training Load stored on the register of the resident memory and calculating the third index based on the recovery values stored on the register of the resident memory. Then the amount of data stored in the resident memory is relatively small.

Preferably the value of injury risk is a numerical value. Numerical value is simple to display and requires very small amount of space in the display.

According to an embodiment the calculation of third index includes steps of measuring heart beat data and analyze a Quick Recovery Test score using ETE library, using the personal history of preferably 1 year of Quick Recovery Test scores to determine personal limits and calculate a personally scaled QRT score for the measurement according to these limits using Sports THA, i.e STHA library, calculating an average of the three most previous scaled QRT scores using STHA.

According to an embodiment the calculation of third weighting factor includes steps of taking the three most previous scaled QRT scores from previous 14 days and calculating a time based weight for each of them according to the fourth weight function ($f\_w_4$), calculating an average of the weight using STHA library and calculating the result based weight for the average scaled QRT.

Surprisingly it has been empirically found that the effect of Recovery test after weighting is preferably 45-55% of the value of the injury risk and a sum of the STTL and ratio of STTL/LTTL correspondingly 45-55% of the value of the injury risk. When there is good coverage of the data for training load and recovery, it causes the training aspect and the recovery aspect both to have an approximately 50-50% effect on the risk. When the coverage is not so good, then the weighting functions correct the situation.

The purpose of the apparatus according to the invention can be achieved with an apparatus for determining injury risk of a user from plurality of exercises using a device with a heart rate sensor, the device having a processor, memory having a resident memory, an output device and software, the software being arranged to monitor each exercise using the heart rate sensor and to determine chosen exercise characteristics of each executed exercise and store them in a resident memory. In addition the software is arranged to calculate Short Term Training Load (STTL) and Long Term Training Load (LTTL) as a result using the determined characteristics stored in the resident memory, wherein the chosen exercise characteristics includes a timestamp and a value depicting a training load of the exercise. The software is also arranged to present the result to the user in the output device. The software is adapted to perform a HRV-based Recovery Test frequently obtaining Recovery values with a time stamp and store each Recovery value in the register of the resident memory with a second timestamp. The software is arranged to calculate indices depicting Short Term Training Load (STTL), ratio of Short Term Training Load (STTL) and Long Term Training Load (LTTL), and Recovery (RI) based on the values stored on the register of the resident memory. The software is further arranged to calculate weighting factors for each said index, each weighting factor depicting the relevance of corresponding index to the probability of injury, correcting each index with corresponding weighting factor to obtain weighted indices and calculate a numerical value of Injury Risk using the weighted indices.

With the apparatus according to the invention the evaluation of injury risk can be automated and measurement of training load during exercise and recovery can be used to derive a simplified result for the value of injury risk. The calculation requires very little input from the user and can be implemented using relatively limited resources, for example with a wrist top device.

The apparatus can be one of the group: heart rate monitor, fitness device, mobile phone, PDA device, wrist top computer, tablet computer or personal computer. Any one of these apparatuses has enough CPU capacity and memory for the calculation of the value of injury risk.

According to an embodiment the software includes a basic library (ETE) for monitoring the exercises and determining characteristics of the plurality of exercises in a host process using a dynamic memory, the characteristics being preferably at least the timestamp and a value of Training load, and for storing the exercise characteristics in a resident memory, and an auxiliary library software (STHA) to determine the injury risk as a child process using characteristics in the resident memory. By using ETE and STHA libraries in the calculation the amount of data stored in the resident memory is reduced and therefore less capacity is required.

Preferably a dynamic memory in a RAM memory is allocated 100-400 bytes (×8 bits) for calculation of injury risk in a child process.

Preferably the register is a database inside the resident memory dedicated for storing characteristics generated by the ETE library.

In one embodiment the host system uses ETE and Sports THA-libraries (STHA), where the ETE is a real-time heart rate analysis library, and STHA is a training history analysis library. STHA-software is called and executed temporarily to calculate injury risk value. The use of ETE and STHA enables minimizing the demand of resources—particularly RAM memory, and more specifically dynamic memory—by selecting key variables suitably. The demand of resident memory is very limited, when only characteristics of each exercise are stored. These include for example time stamp, TRIMP (Training Impulse), EPOC, Training Effect, Absolute Recovery value and so on. The injury risk calculation uses training history data for all kinds of exercise types (e g running, bicycling, rowing, gym exercises etc.). The calculation analyzes absolute training load and saves it to internal memory.

Preferably, there is a 28 days training history available, and a minimum 7 days. The system will typically store and take into consideration up to 365 days (1 year) of training history data.

It can be seen from the literature on physical training that the harder the training has been, the more the homeostasis of the body is disturbed. The more that the homeostasis can be disturbed, the greater the adaptations that can be created in the body and the improvements in physical condition that derive from the adaptations. Thus, the variable of the training load may be a peak value regarding training effect measured as disturbance level of homeostasis. As a person with greater fitness level needs greater training stimulus, the training load can be scaled to each individual's capabilities in order to depict training effect.

Recovery can be measured with an analysis of HRV. As HRV values are very individual, the recovery values can be personally scaled by considering the typical values and range of HRV for each person. Scaling of personal training load and recovery can be calculated by the STHA library.

Injury risk is determined based on three main parameters: a HRV-based recovery value, current short-term training load, and change in short-term training load relative to long-term (chronic) training load. Injury risk calculation analyzes previous training data; current training load, training load changes and variation in recovery level during different days. Injury risk can be calculated at any time point as long as there is information on the current training load, and it combines the information from available parameters.

The following terms are used in the application:
Short-term (acute)=3-10 days
Long-term (chronic)=14-28 days
Injury Risk=A numerical value calculated based on the user's training history depicting user's statistical probability of getting injured during next exercise expressed as a value of a range having a first end depicting very small probability of getting injured and second end depicting a high probability of getting injured.

These are exemplary definitions.

In one exemplary embodiment, a method for determining injury risk may comprise following steps (see FIG. 1):
  chosen exercise characteristics of each executed exercise are determined using measured heart rate data in the memory, and
  after each exercise the determined characteristics of each executed exercise are stored in a memory, the chosen exercise characteristics including values of at least following variables:
  a date of the exercise,
  a recovery value from the exercise
  a value depicting a training load of the exercise
  using the stored exercise characteristics, the following calculation steps may be performed, and will be described in further detail below:
  1) Calculation of short-term (acute) training load during the last 3-10 days, wherein the short-term load can be for example
    total TRIMP sum of the last 7 days
    a sum of a weighed sum of excess post-exercise oxygen consumption (EPOC) based training load taking into account at least one of aerobic and anaerobic training load of the last 3-10 days.
  2) Calculation of long-term (chronic) training load during the last 28 days (1 month) representing typical workload during one week with last month.
    a one week of training history may already yield result since one-week result may be extrapolated to represent a typical week
  3) Calculation of the ratio between short-term and long-term training load (acute vs. chronic)
    it may be required that certain amount of exercise sessions, for example 3, has been performed during a week to be considered in the calculation of ratio between short-term and long-term training load.
  4) Calculation of Recovery Status during the last 14 days (using Quick Recovery values)
    In the calculation of QRT result the absolute heart rate and HRV based results may be scaled on the scale of 0-100 based on the average and standard deviation of the personal QRT measurement history.
    Maximum length of the history used for calculating average and standard deviation of the result for the person may be up to one year, for example.
    If several measurements are performed each day, the average of all personally scaled QRT values for one day may be used 5) Defining an index as a score of 0-100 for each of the components (short-term load, short to long-term training load ratio, recovery) using scaling functions with linear dependencies on the optimal as well as poor end and good end results for each component.
6) Defining a weighting factor for these indices.
   Each weighting factor is derived by using a weighting function
   The weight of short- to long-term training load ratio depends on how many weeks has been accepted for long-term training load calculation, full weight is got when there are 3-4 weeks of training history.
   The weight of Recovery depends on two factors:
      how long time has passed from last measurements within the 14-day window; the more distant the measurement(s) the lower the weight
      what is the recovery state; poor results increase weight of recovery for overall score.
7) Calculating overall injury risk result based indices for different components using the weighting factors
   Injury risk is the weighted result of the available components of it
8) Defining reliability of the score by summing the second and third weighting factors. This reliability is expressed as poor-moderate-good. If there is limited amount of data, reliability of the results decreases.
9) Providing user feedback of the overall injury risk value with a 0-100 scale, and visual, and verbal classification for that.
10) Providing user feedback of the components of the injury risk (short-term training load, short-term to long-term training load ratio, and recovery) with scores, visual, and verbal way.
11) Providing user information on the reliability of the results.

BRIEF DESCRIPTION OF THE DRAWINGS

Advantages of embodiments of the present disclosure will be apparent from the following detailed description of the exemplary embodiments. The following detailed description should be considered in conjunction with the accompanying figures in which the figures may show exemplary embodiments of the method and apparatus for determining injury risk. Figures are only exemplary and they cannot be regarded as limiting the scope of invention.

FIGS. 5a-5d shows example feedbacks present of the injury risks for a team, FIG. 6 represents example feedback on the injury risk for an individual athlete.

The following table shows some exemplary definitions and abbreviations of terms used in the exemplary embodiments described herein.

| Term or abbreviation | Definition |
| --- | --- |
| HR | Heart rate (beats/min) |
| HRmax | Maximum heart rate (of a person) (beats/min) |
| VO2 | Oxygen consumption (ml/kg/min) |
| Physical Readiness | Fitness level or recovery state parameter depicting user's ability to exercise |
| VO2max | Fitness level, maximum oxygen consumption capacity of a person (ml/kg/min) |
| Training Load | A measure of the amount of training a person has performed, and may take various forms. One can measure training load in a single session, or cumulatively over a period of time. More or harder training will have a higher training load. There are short (ACUTE) and long-term training load. |
| TLR | The ratio between long-term and short-term training load |
| HRV | Heart rate variability meaning the variation in time interval between successive heart beats. The magnitude of heart rate variability may be calculated from electrocardiographic or photoplethysmographic signals, for example. |
| EPOC | Excess post-exercise oxygen consumption. As it can be nowadays estimated or predicted - based on heart rate or other intensity derivable parameter - it can be used as a cumulative measure of training load in athletic training and physical activity. |
| TRIMP | Training Impulse score. A cumulative measure of the impact of a training session |
| Recovery state parameter | A parameter depicting how well person or athlete has recovered from prior training. A recovery state parameter may be based on measured heart rate and/or heart rate variability (HRV). Recovery state can be evaluated also using, for example, sleep quality, as overtraining may provoke sleep disturbance. |

DETAILED DESCRIPTION

Figure 1A:
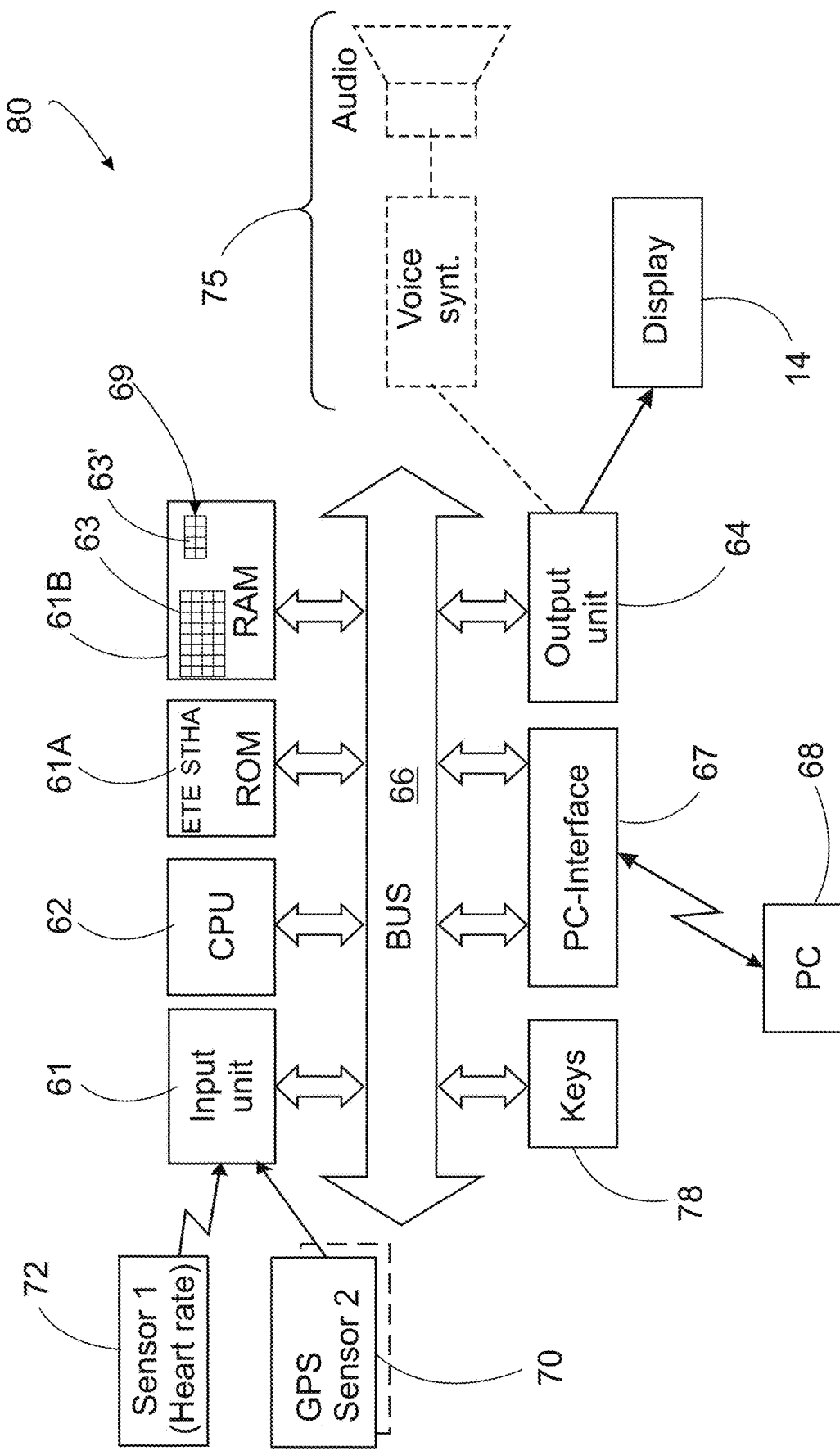
FIG. 1a represents an example of a hardware assembly.

The method for determining injury risk is implemented using an apparatus according to invention including a device 80 shown in FIG. 1a. Device 80 includes a heart rate sensor 72, a data processing unit 62 and a memory 61A, 61B. The heart rate sensor 72 is configured to measure the heartbeat of the person, the heart rate signal being representative of the heartbeat of the user. The data processing unit 62 is operably coupled to at least heart rate sensor 72. The memory 61A, 61B is operably coupled to the data processing unit 62 and the memory may be configured to save background information of a user, for example, background data including an earlier performance level, user characteristics, and the like. Optionally the device may include at least one sensor 70 to measure an external workload during an exercise, which sensor 70 is operably coupled to the data processing unit 62. More details about hardware implementation of the method and the system according to the invention are described later in this application.

Figure 1B:
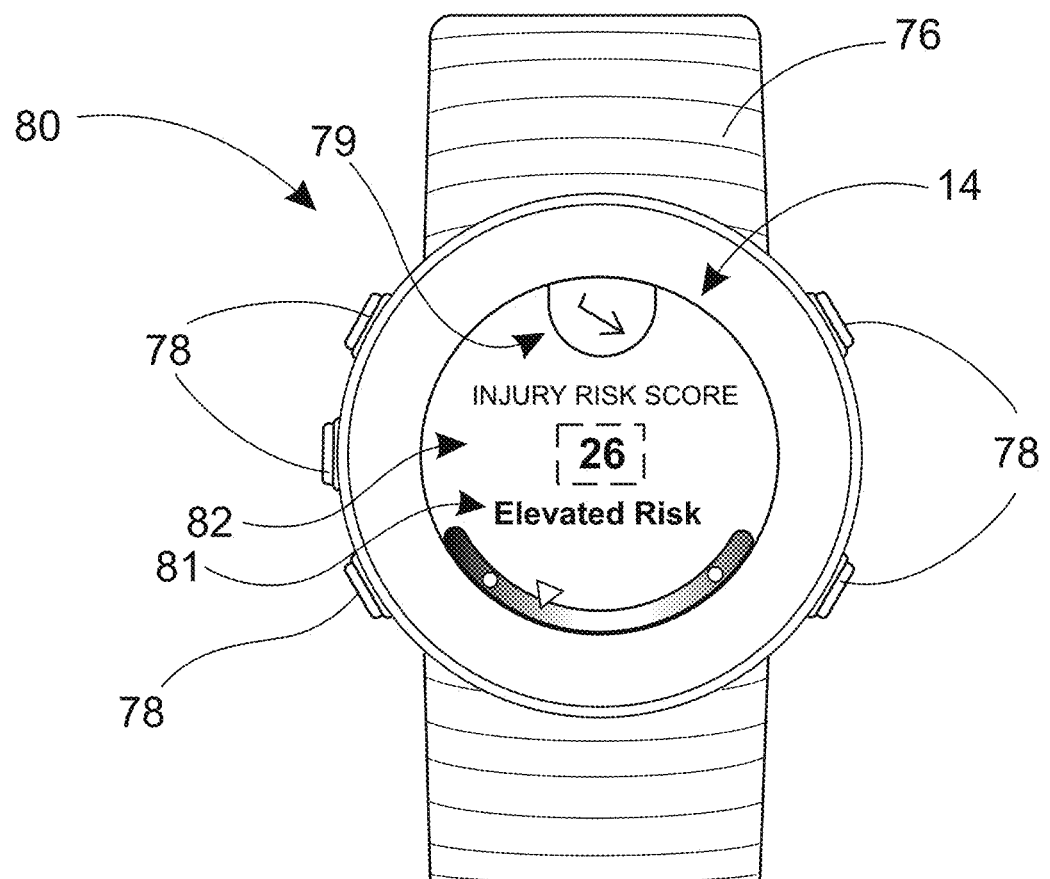
FIG. 1b, shows an example of showing injury risk to a user on a sample wrist-top device
Figure 2:
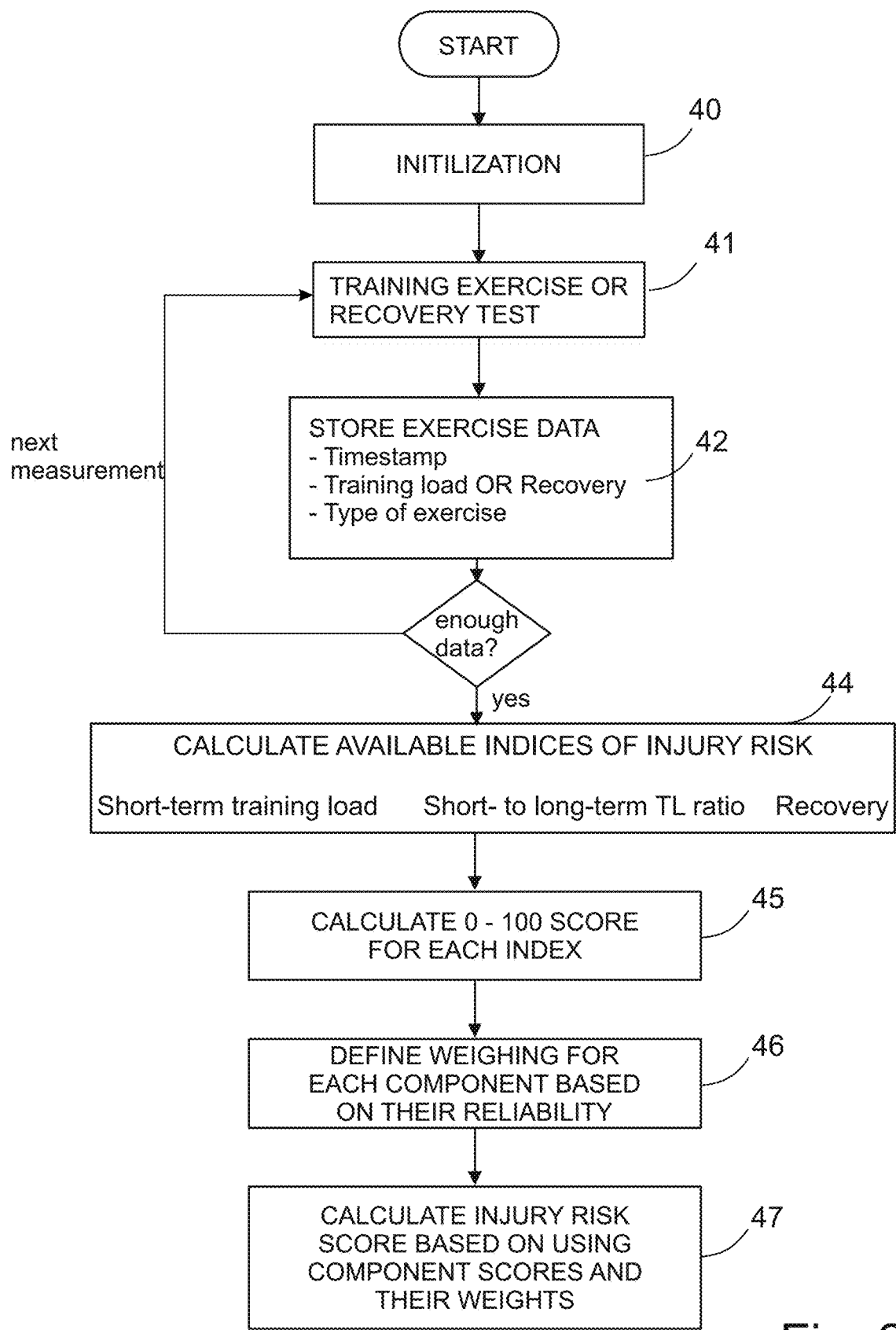
FIG. 2 shows an analysis process of the injury risk.

A further illustrative example of the presentation of the injury risk calculation is shown in FIG. 1b showing on a wrist top device 80 (worn on the wrist of a user held on the wrist by a strap 76) forming a user interface and used by a conventional fitness enthusiast or sportsperson. It has a display 14 with several fields. The result, the actual value of injury risk is shown literally in the field 82 and graphically in the field 79. The injury risk may optionally have further screens similar in presentation, for example, as those shown in FIGS. 5a-5d, that may be scrolled through to see further elaboration of the injury risk information or each of the components. Buttons 78 can be used to initiate recording of training as well as Recovery Test. In addition a short verbal commentary 81 may be included in order to clarify the meaning of the Injury Risk value 82. An additional symbol 79 may be included to indicate trend of injury risk value, i.e whether the risk is increasing or decreasing.

The determination of injury risk is based on three main parameters, a HRV-based recovery value, current short-term training load, and change in short-term training load relative to long-term (chronic) training load. Calculation of both short- and long-term training load is done using collected training information. Short-term (acute) training load is preferably collected over the past seven days, and may be represented by a total TRIMP (training impulse sum) of the last seven days, a sum of excess post-exercise oxygen consumption (EPOC) based training load which may also consider both aerobic and/anaerobic training load or another similar training load measurement. If multiple workouts occur on the same day, then those workouts are also added together to create a total training load for that individual day. Short-term training load may be calculated as an overall sum of all training load during the last 3-10 days or alternatively by weighted sum considering the proximity of training sessions in a manner where the less distant training sessions (e.g. those performed 1-2 days ago) may have more effect on the short-term training load value than the more distant (e.g. those performed 6-7 days ago) training sessions. TRIMP is the preferred value, because this is mostly for professional sports use cases where TRIMP is a key metric for training load. In implementation oriented for ordinary people EPOC (or EPOC and TRIMP combined) is preferably the training load metric.

Long-term (chronic training load) is preferably represented by the last 28 days. It may be calculated as the average short-term load of the last 4 weeks, and may represent a typical one-week training workload within the last month. It may be possible, therefore, to extrapolate a chronic training load measurement after one-week of training history is collected. It should be evident, however, that increased amount of long-term training data will create a more accurate representation of a typical week from the past month. At a minimum, there should be at least three exercises in total within the last 4 weeks to enable a long-term training load calculation.

The short-term to long-term training load ratio (TLR) thus serves to compare recent training load to the typical one-week training load over the past month. In some embodiments, it may be required that a minimum number of exercise sessions have been performed during a week to be considered in the calculation of the ratio between short-term and long-term training load. The ratio is calculated by simply dividing the STTL value with the value of LTTL.

The calculation of recovery status over the last 14 days may be done using any number of known recovery tests that use heart rate or heart rate variability to determine a recovery value. One such example is to use a Quick Recovery Test (QRT) score, i.e. recovery value which utilizes absolute heart rate and heart rate variability-based results. The test results may also be personalized based on a scaling of previous QRT results. If multiple recovery measurements are performed in a single day, an average of all of the resultant QRT values that have been calculated based on the personal scaling may be used. The scaling of previous QRT results is based on the average and standard deviation of recovery data from as far back as the past year, when available.

As an alternative to QRT, sleep-time measurement could be used for recovery assessment. A standard period could be utilized for recovery assessment by calculating recovery index during sleep from a 4-hour period starting 30 min after detected start of sleep period, i.e going to bed. Optionally recovery could be analyzed from some specific sleep stage, for example from so called slow wave sleep/deep sleep.

As a further embodiment recovery can be assessed using a combination of several ways to define recovery. One option is to measure recovery during training session already, for example by assessing heart rate recovery where a personally rapid drop in heart rate after or between activities or burst of activities is a sign of good recovery.

The Quick Recovery Test is a HRV-based done using the ETE library. The duration of the QRT is 1-10 minutes, preferably 2-4 minutes. The short duration of the QRT makes easy to use. Steps of the Quick Recovery test are a) measuring beat-by-beat HR for 3 min, b) using QRT formula to get an absolute QR value from HRV and HR and c) scaling the values with personal QRT history using the average and standard deviation of the result for scaling.

Figure 3A:
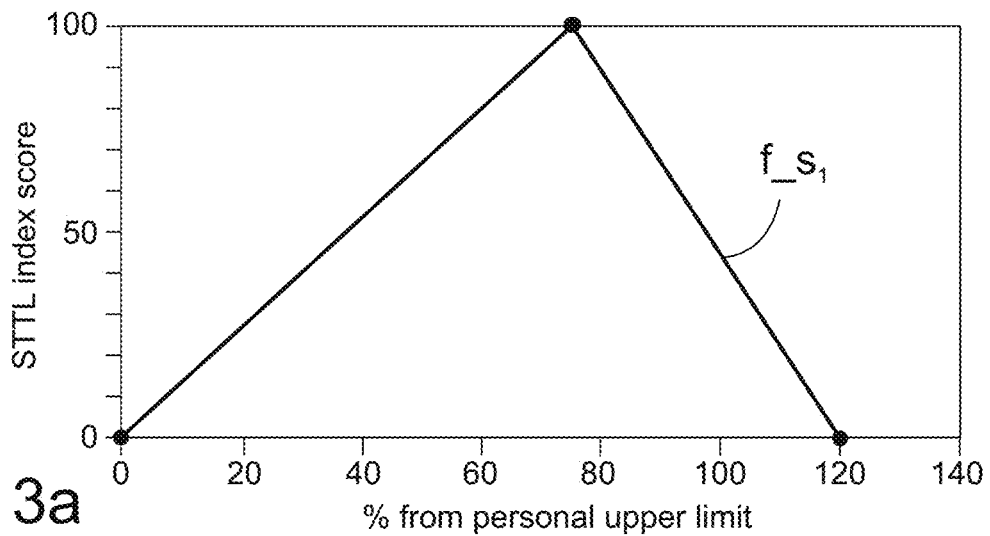
FIGS. 3a-3c show graphs which are used for determination of scores for different components of the overall injury risk.
Figure 3B:
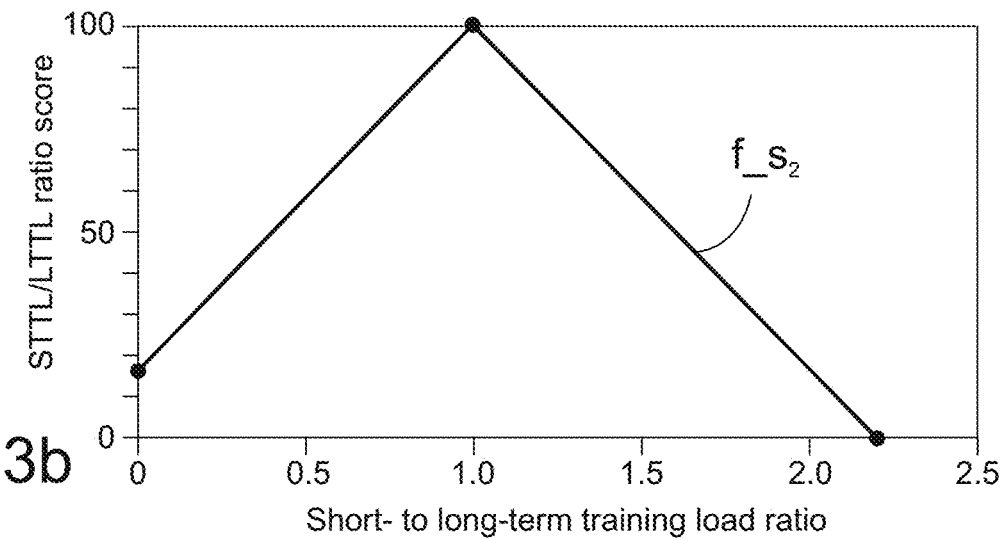
Figure 3C:
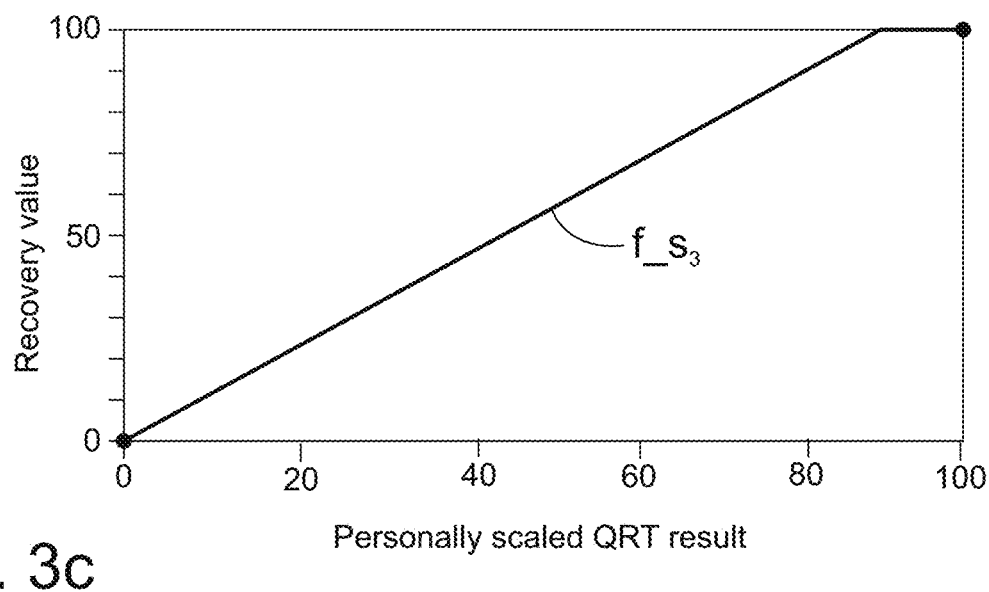

Each of the components, namely short-term training load, short-term to long-term training load and recovery status are converted into indices defined as a score 0-100 using scaling functions with linear dependencies the optimal levels as well as the poor and good ends of each component. FIGS. 3a-3c illustrates an example of the dependency functions relating to each component and their score. FIG. 3a shows a graph of the first scaling function $f\_s_1$ which can be used to calculate a first index score on a scale of 0-100 using the measured STTL indicated as a percentage from the personal upper limit of the user. By plotting the percentage to the first scaling function the first scaling function will give a result of the first index. FIG. 3b shows a graph of the second scaling function $f\_s_2$ which can be used to calculate a second index score on a scale of 0-100 using the measured STTL and LTTL ratio. FIG. 3c shows a graph of the third scaling function $f\_s_3$ which can be used to calculate a third index score on a scale of 0-100 using the measured Recovery values indicated. It should be understood that these scaling functions may also be changed to reflect, for example, different users, different activities, or other variables that effect the activity expectations of different sports. In other words, for example, scaling of each measured value of short-term training load is done by calculating the scaled value using the first scaling function of short-term training load.

Figure 4A:
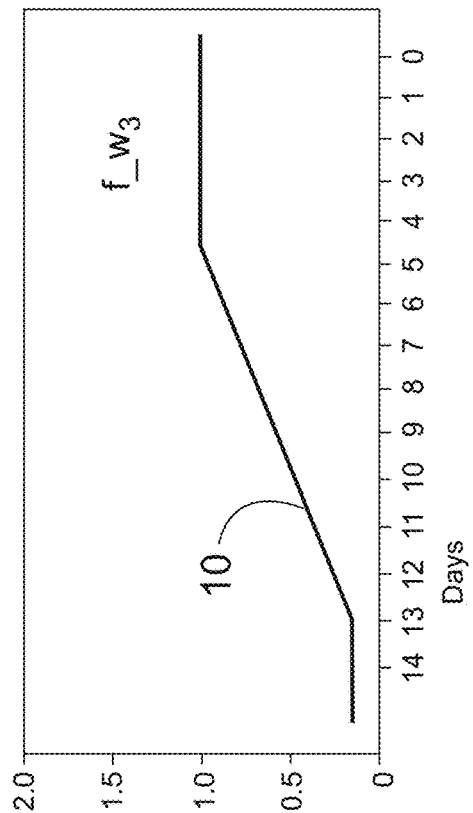
FIG. 4a-4d show graphs of weighting factors for different components of the overall injury risk score.

Each index is also given a weighting factor. The weighting factors are based on a variety of criteria related to each index. Each weighting factor is calculated using a weighting function shown in FIGS. 4a-4d. The weighting factors could also be modified to suit particular sports or contexts:

The first weighting factor for short-term load is calculated using a first weighting function f(w1) shown in FIG. 4a. The first weighting factor remains constant. In an exemplary embodiment, because short-term training loading is represented by a total training load for the entire seven days, no single day is weighted less or more than another during the entire week.

Figure 4C:
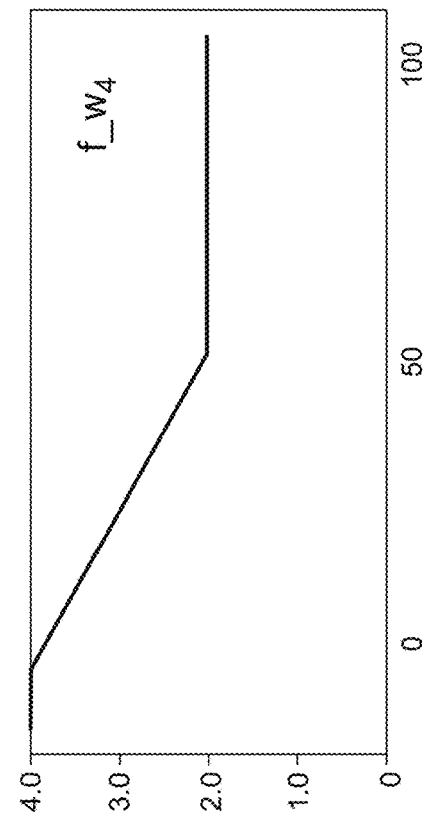
Figure 4B:
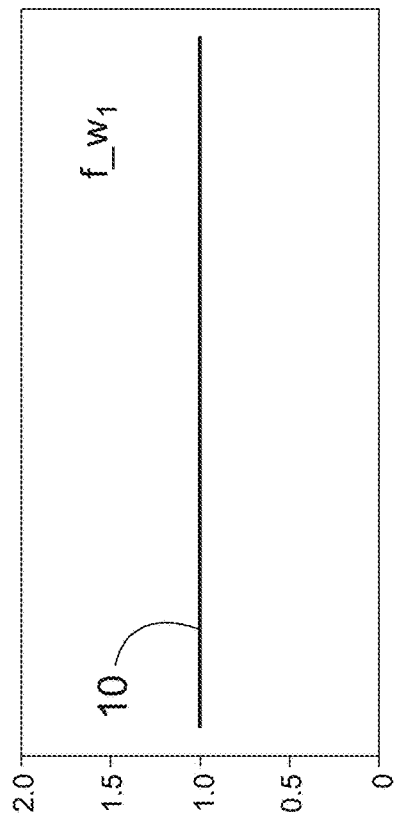

The value of the second weighting factor of the short- to long-term training load ratio is calculated using a second weighting function (f(w2)) shown in FIG. 4b. The second weighting factor depends on how many weeks have been accepted for long-term training load calculation. The second weighting function gives the lowest value for the second weighting factor when there is less than a single week of training data available or an approximate extrapolation calculation on less than 7-days training has been made. Partial weighting may be provided when there is 2-weeks of training history available, and full weight is given when there is at least 3 weeks of training history available.

Figure 4D:
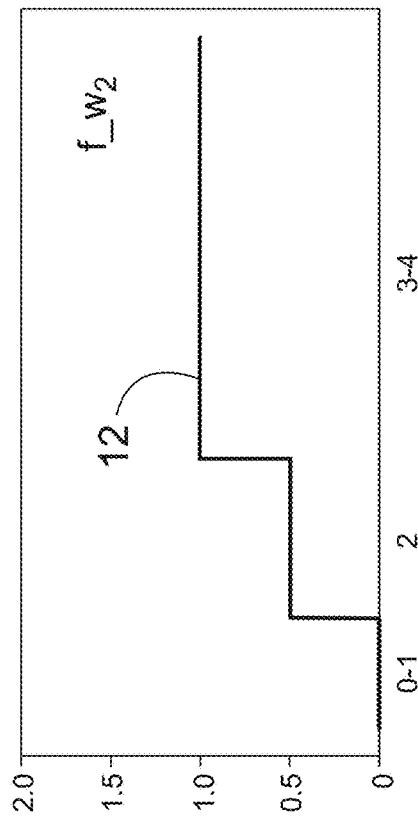

The third weighting factor of the recovery values depends on a fourth and a fifth weighting function:
  i. FIG. 4c shows the fourth weighting function (f(w4)) the value of which depend on how much time has passed since the most recent recovery test measurements within the 14-day window; the more distant the measurement(s) the lower value of the fourth weighting function. For example, if the most recent recovery test was performed 10 days ago, it will contribute less weight to the injury risk calculation than one that was performed 2 days ago.
  ii. FIG. 4d shows the fifth weighting function (f(w4)) the value of which depend on current recovery state; the recovery test results from the previous 3 measured days (or fewer if 3 measurements are not available) are averaged to determine the value of the fifth weighting function. In an exemplary embodiment, values lower than 50% progressively have increased weighting.

An overall injury risk result is then determined based on the component scores i.e indices, presented as 0-100, and the weighting factors. The resultant injury risk value is the weighted average of the indices.

The reliability of the injury risk value is calculated, by determining reliability for each of the indices. Reliability is generally expressed on a scale of poor-moderate-good and primarily reflect the amount of data that is available to make each calculation.

The different components and the overall injury risk is given a reliability results as follows:
  1. Short- to long-term training load score reliability
     Weight=0.0→poor
     Weight=0.5→moderate
     Weight=1.0→good
  2. Recovery value reliability
     Weight>=0.0→poor
     Weight>=0.15→moderate
     Weight>=1.0→good
  3. Overall injury risk score reliability=sum of items 1 and 2
     Weight>=0.0→poor
     Weight>=0.5→good The reliability score for each index is the weighting factor of the corresponding index. In other words, the overall injury risk reliability is preferably the sum of second weighting factor and third weighting factor.

The resultant injury risk calculation may be presented to a user in a variety of ways depending on the apparatus used. Initial feedback may include showing a numerical injury risk value given on a 0-100 scale. Exemplary embodiments of presentation of injury risk are shown in 5a-5d and 6. Table 1 below shows a number of basic text alternatives for describing injury risk or each of the components. This could be shown, for example, numerically, using an absolute value or a normalized value such as a percentage or a rating, or possibly in text, such as sectioning each score into a "low", "moderate", or "high" score. The corresponding longer description of each status may accompany the feedback, depending on the space available. FIGS. 1a and 1b are illustrative examples of how this feedback may presented on different devices.

TABLE 1

Feedback sentences for different components and the overall injury risk score

| Injury risk Feedback Number | Injury risk score | Score Feedback |
| --- | --- | --- |
| Risk1 | 0-29 | Elevated injury risk |
| Risk2 | 30-59 | Moderately balanced training state |
| Risk3 | 60-89 | Balanced training state |
| Risk4 | 90-100 | Very balanced training state |

| Feedback Sentence Number | Indicative short- to long-term TL ratio | Feedback Sentences |
| --- | --- | --- |
| Ratio1 | 0-0.5 | Training load decreasing very sharply compared to training history |
| Ratio2 | 0.51-0.74 | Training load decreasing compared to training history |
| Ratio3 | 0.75-1.5 | Short and long-term training load is optimally balanced |
| Ratio4 | 1.51-1.8 | Training load increasing faster than recommended |
| Ratio5 | 1.81- | Training load increasing very sharply which increases a risk for injury |

TABLE 1-continued

Feedback sentences for different components and the overall injury risk score

| Feedback Sentence Number | Indicative short-term TL relative to personal upper limit | Feedback Sentences |
| --- | --- | --- |
| STL1 | 0-22% | Training load is very low which do not support building fitness and resilience |
| STL2 | 23-45% | Training load is low at the moment |
| STL3 | 46-93% | Training load is sufficient to build fitness and resilience |
| STL4 | 94-107% | Training load is high at the moment |
| STL5 | 108%- | Training load is very high at the moment which increases a risk for injury |

| Feedback Sentence Number | Indicative weighted Quick Recovery Test score, i.e recovery value from last 14 days | Feedback Sentences |
| --- | --- | --- |
| R1 | 0-15% | Recovery and readiness is very poor |
| R2 | 16-29% | Recovery and readiness is poor |
| R3 | 30-54% | Recovery and readiness is at moderate level |
| R4 | 55-81% | Recovery and readiness is sufficiently good |
| R5 | 82-100% | Recovery and readiness is optimal |

FIGS. 5a-5d are illustrative examples of how training status may be shown to a user which may be displayed on an ordinary computer device having a host system for physiological measurements and analysis. The amount of information may vary based on the physical space available on the display, and may, for example, be displayed on multiple pages. In this example, a text "injury risk" level is shown at the top with a graphic representation of the injury risk scores calculated over time. Each component of the injury risk score is shown below with a brief text feedback text. All of this information is derived from STHA and examples of possible text descriptions were shown in Table 1.

As shown in FIG. 6, an average injury risk may also be presented when multiple users are being monitored at once or the collected data is transferred to a centralized system. An average based upon each individual player's injury risk score may be presented. Athletes who are in particular injury risk zones that require attention may be flagged the system so that coaches and trainers may be aware of which players may require extra recovery or adjusted training. Similar team status analyses may be presented for each of the respective injury risk components (not shown).

Although the embodiments described in the detailed description disclose that a high Injury Risk value indicates the user's low probability of getting injured, it should be understood that the calculation and presentation of injury risk can also be implemented in opposite manner. This means that low injury risk value can indicate the user's low probability of getting injured if scaling functions are defined differently. Both implementations are equal solutions.

Data collection devices that do not have a display, such as some fitness tracking devices, heart rate belts without a display, or other HRV collection devices without a display may also transmit the collected data to external devices, such as smartphones or computers. In these cases, when available, audio feedback may be provided through speakers or through headphones.

In addition to the feedback, users may also be presented with reliability information. As noted above, a typical way of presenting reliability to a user may be in the form of "poor-moderate-good". Additional feedback may also be given to provide a brief explanation of how a user may increase reliability for future measurements, such as by increasing the number of recovery tests performed.

The current state of art already enables calculation of "sprinting time" in different training sessions (see applicant's patent application US2017143262). Acute and chronic training load (EPOC and/or TRIMP) may also be "boosted" based on cumulative time spent above VO2max intensity (i.e. sprinting time). For example, if the previous 7 d time period has included lots of time spent above VO2max intensity—meaning for example sprint and speed endurance training—calculated short-term training load value can be multiplied according to predetermined criteria.

Sprinting time could also be used as a separate factor in injury risk calculation as sprinting time and sprinting distance have well known relationship with injury risk. As applicant's patent application US2017143262 enables differentiation of supramaximal intensities (intensities above VO2max) time spent at different supramaximal intensities could have different effect on injury risk: E.g. 500 seconds spent at 150% VO2max intensity could have bigger impact on injury risk as 500 seconds spent at 130% VO2max intensity.

There are many other components of fitness that may affect injury risk in a similar way. Other components of fitness, such as those related to aerobic or anaerobic work, speed or speed endurance, or power and power endurance, may also affect short-term training load in a specific way to characterize increased injury risk. Additionally, an analysis of the balance between these specific components of fitness being focused on during training may influence injury risk if it is determined that excess time is spent being on that particular system. For example, repeated power workouts may increase injury risk. Specific rules may be set so that workouts that occur within proximity of each other also increase the training load value according to predetermined criteria.

Environmental factors may also affect injury risk. Athletes that train in unusually hot or cold weather or at altitude tend to fatigue more quickly than at temperatures they are otherwise accustomed to. The body works harder at higher altitudes, for example, than they may experience a higher training load even when performing an identical workout that was done at lower altitude. Predetermined criteria may also be applied in these situations to increase short-term training load to reflect these extreme conditions.

Subjective feelings of fatigue are also well-known as a useful measure of fatigue. The system may alternatively ask participants for a subjective fatigue score that may affect the injury risk calculation. Such scores may increase the training load score from a particular session, or may increase the injury risk by a fixed value, particularly on occasions where no training session is performed but a subjective fatigue measure is still provided.

According to an embodiment total daily step count may be also affect injury risk. The total daily step count can be regarded as additional load information.

Any additional context that affects the Injury Risk described above may be taken into account in the calculation of Injury Risk as a separate multiplication factor that is used for multiplying the Injury Risk score. For example, different contexts may have different multiplication factors ranging from 1.01 to 1.30. Another embodiment is to consider the additional factors presented above as independent components or indexes of the Injury Risk calculation having their own weighting on the Injury Risk score. Still another embodiment is to consider the additional factors affecting Short Term Training Load and Long Term Training Load values. For Example, a power workout that is performed on a day after having a previous power workout on the day before can multiply the training load value by 1.05. Similar principle applies for example to sprint training: sprint training may be used to multiply Short and Long Term Training Load by 1.20, and/or the amount of sprint training can be followed up in short term (3-10 days) and long term (14-28 days) window to be used as independent factor for Injury Risk. In the latter case, the ratio of sprint training in short and long term window can formulate an independent index of 0-100 and have a weight of 0.5 on the Injury Risk.

The method could be implemented in any device comprising a processor, memory and software stored therein and a user interface, for example, a heart rate monitor, fitness device, mobile phone, PDA device, wrist top computer, and the like. The implementation can be done in an embedded system using only small amounts of RAM memory and CPU time.

The above results can be given to individuals and teams. In the latter the individuals can be shown to belong to different injury risk categories (who are at most risk for an injury) as well as the average result for the team, as shown in FIG. 6. Each individual's scores displayed within in a team context are shown as their personalized and scaled scores of Injury Risk.

Regarding short-term training load, a personal scaling can be performed for example by calculating:
1. Short-term training load being the TRIMP sum during the last 7 days
2. Defining the personal upper limit (maximal) load based on training history, being the highest short-term load found from the training history from up to one year of data
   a. If acute load gets higher than the last maximum acute load value, increase it to the closest 100-round figure that is above the acute load.
   b. The upper limit may be decreased by for example 100 when:
      i. Short-term load has been lower than maximal load minus 100 for the last two weeks and there is over a 14 days of training history data
   c. Maximal short-term load limit value may be limited to a predetermined value, for example over 500 units of TRIMP. It may be the case that the predetermined value can also be used even when there are no training sessions in the history Recovery test status may also be personalized. In the case of using a Quick Recovery Test, the personalized scaling is preferably performed using a person's recovery test data, using all available test data from up to the previous year. The average and standard deviation from all of the values in the person's recovery test history is calculated.

According to an embodiment the calculation of weighed third index has the following steps, wherein the exercise data is measured, an absolute QRT value is analysed from the measured exercise data using ETE library and personal limits of the user are determined using personal history (1 year) of absolute QRT values. Then a personally scaled QRT value is calculated for the measurement according to these personal limits using STHA library. A daily average of the personally scaled QRT values is taken using STHA library and three most previous daily average QRT values from previous 14 days are taken and a time based weight for each of them according to the fourth weight function is calculated using STHA library. If there are not at least three days with QRT measurements in that 14 day window, no further results can be calculated. Next the average of these three daily QRT values is calculated using STHA library, the average of the weights is calculated using STHA library and a result based weight is calculated for the average scaled QRT using fifth weighing function with STHA library. The final QRT score is calculated by applying the third scaling function to the average of the three daily QRT values using STHA library.

Personal scaling of STTL or QRT or both will increase the accuracy of the method by taking into account the user personal training history and heart-rate upper limit already into ETE calculations.

Figure 7:
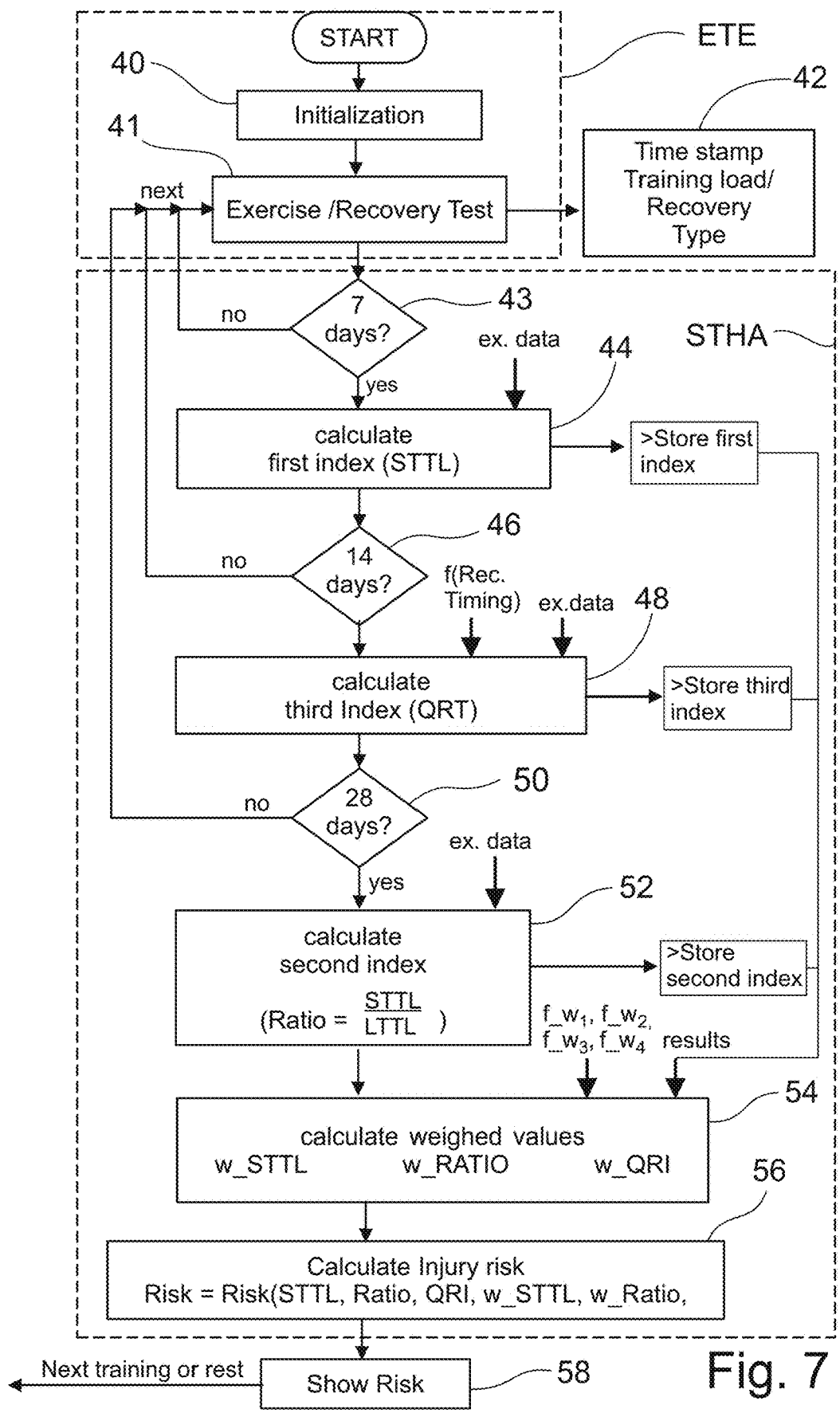
FIG. 7 shows a detailed flowchart of the process of calculation.

Regarding FIG. 7 the host process is continuously running by a host system. After, a start software initializes at step 40 the child process (i.e. calls STHA) and populates background data in runtime registers. When an exercise starts the host process calls specific software from the library ETE, which takes care of ordinary calculation and monitoring of exercises and calculates desired physiological results, including characteristics of each exercise. Each exercise is monitored in step 41 and after that the characteristics, i.e. the values of specific parameters are stored to a resident memory in step 42. Those specific parameters are date, training load or recovery and a type of the exercise (Quick Recovery Test or physical exercise). While training load values are obtained by ordinary exercises there should be carried Quick Recovery Tests frequently obtaining Recovery value.

In a step 43 there is a check whether there is enough exercise data for calculation of training Short Term Training Load (STTL-value) in Step 44. If it is determined in step 43, that the number of exercises is too low, the execution returns to monitor the next exercise. The calculation of Injury Risk can proceed with even without calculation of STTL value, but preferably there are at least two exercises that have been measured.

The calculation of STTL in step 44 is based on the training load exercise data stored in the resident memory. The absolute STTL-value, in an exemplary embodiment described by a cumulative training load measure, is scaled and the scaled first index is stored as a value between 0-100 in step 45.

In step 46 there is a check whether there is enough recovery values data for calculation of the third index of step 48. If it is determined in step 46 that the number of recovery values is too low, the execution returns to monitor next exercise. An adequate amount of data on recovery is at least three Recovery Tests from the last 14 days.

The calculation of the third index, i.e., Quick Recovery Index in step 48 is based on both the recovery data and the time stamp of each recovery test. The calculated value of the third is scaled and stored as a value between 0-100 in step 49.

In a step 50 there is a check whether there is enough data for calculation of Long Term Training Load (LTTL-value) of step 52. If there is insufficient data, the execution returns to monitor the next exercise. An adequate amount of data for LTTL-value calculation is at least three exercise sessions from the last 7 days. In FIG. 6, "ex-data" shown in in steps 44, 48 and 52 is an abbreviation of exercise data.

The LTTL ratio value calculated in step 52 is used to calculate a training ratio based on STTL/LTTL and is scaled to become the second index having a value between 0-100. This value i.e. the second index is stored in step 53 to be used in later steps. At this stage in a resident memory there are the indices of STTL, QRI and Ratio, namely the first index, the second index and the third index, all in a scaled value of 0-100.

In step 54 the weighting values of indices of STTL, QRI and Ratio are calculated using weighting functions $f\_w1$, $f\_w2$, $f\_w3$ and $f\_w4$ shown in FIGS. 4a-4d. The resulting weighting factors are the first weighting factor $w\_STTL=f\_w1=1$, the second weighting factor $w\_Ratio=f\_w2(weeks\_LTTL)$ and the third weighting factor $w\_QRI=<w\_QRT>*f\_w4(<QRT>)$, where weeks_LTTL is the number of weeks of training history used in the LTTL calculation, and $$<w\_QRT>=(f\_w3(t\_QRT\_1)+f\_w3(t\_QRT\_2)+f\_w3(t\_QRT\_3))/3$$

is the average of QRT weights, where $t\_QRT\_j$ is the time since the last QRT value, and $<QRT>$ is the average of the last three QRT values. Note that the weight of STTL is always 1.

Using these indices and their weighting factors the injury risk is calculated in Step 56 as the weighted average:

$$Risk=(STTL+w\_Ratio*Ratio+w\_QRI*QRI)/(1+w\_Ratio+w\_QRI).$$

In an alternative embodiment, the minimum data requirements described above may be overcome by extrapolating the existing data available, allowing the program flow to continue and provide an injury risk value. For example, the LTTL-value may be approximated by using a single week as approximately representative of a typical week and extrapolate the remaining training data. Similar extrapolations could be made by taking the average of multiple weeks, allowing for increased data to improve the accuracy of the extrapolation. Similar calculations may be made using, for example, at least 3 days of STTL-data, or at least 5 days of recovery test data.

In this alternative embodiment, therefore, a reliability measure may also be given to inform the user of how accurate the injury risk measurement may be based on the existing data available.

In step 58, the injury risk value is shown to the user. As described above, the injury risk value may also be paired with written, visual, or verbal feedback. Depending on the devices used, it may also be possible to display the results of multiple users at once as well as present and average of all of the users. After execution of the injury risk calculation the method may return to the same or next exercise.

Although FIG. 7 shows the diagram of an embodiment of the method according to the invention wherein injury risk is calculated after the exercise has been performed, it must be understood, that the calculation of injury risk can be done even during an exercise. This may be useful when having a long exercise in which the injury risk may rise considerably as the exercise progresses.

The system and method according to the exemplary embodiments can be applied in many kinds of devices as would be understood by a person of ordinary skill in the art. For example, a wrist top device with a heart-rate transmitter, a mobile device such as a phone, tablet or the like, or other system having CPU, memory and software therein may be used.

According to exemplary FIG. 1a, the implementation may include an assembly built around a central processing unit (CPU) 62. A bus 66 may transmit data between the central unit 62 and the other units. The input unit 61, ROM memory 61A, RAM memory 61B including a dedicated memory, i.e. resident memory 63' for a register 69 of the injury risk application and memory 63 for the host system, keys 78, PC connection 67, and output unit 64 may be connected to the bus.

The system may include a data logger which can be connected to cloud service, or other storage as would be understood by a person of ordinary skill in the art. The data logger may measure, for example, physiological response and/or external workload.

A heart rate sensor 72 and any sensor 70 registering external workload may be connected to the input unit 61, which may handle the sensor's data traffic to the bus 66. In some exemplary embodiments, the PC may be connected to a PC connection 67. The output device, for example a display 14 or the like, may be connected to output unit 64. In some embodiments, voice feedback may be created with the aid of, for example, a voice synthesizer and a loudspeaker 75, instead of, or in addition to the feedback on the display. As shown in FIG. 7, the sensor 70 which may measure external workload may be a GPS sensor, although this may be replaced by a number of sensors or different types of sensors, which may be used together to define the external work done by the user.

More specifically the apparatus presented in FIG. 1 may have the following parts for determining an injury risk:

a heart rate sensor 72 configured to measure the heartbeat of the person, the heart rate signal being representative of the heartbeat of the user;

optionally at least one sensor 70 to measure an external workload during an exercise, and a data processing unit 62 operably coupled to the said sensors 72, 70, a memory 61A, 61B operably coupled to the data processing unit 62, the memory may be configured to save background information of a user, for example, background data including an earlier performance level, user characteristics, and the like.

The apparatus may include dedicated software configured to execute the embodiments described in the present disclosure. The training injury risk application requires RAM—memory 100-400 bytes (×8 bits), preferably 120-180 bytes. Each timestamp requires 2 bytes, and in addition the TRIMP sum [16 bits], and Quick Recovery Test average [8 bits] are recorded. In total each day requires 5 bytes all of which is stored to a register. The register is database inside the resident memory dedicated for storing characteristics generated by the ETE library. Generally, calculation has a window of plurality of days, e.g. 20-80 days, preferably 24-36 days.

The low level of RAM memory required is due to the use of the method according to the invention which can be implemented in an embedded device having limited CPU and memory resources and having a host system. In one embodiment the host system uses ETE and STHA-libraries, where the ETE is a real-time heart rate analysis library, and STHA is a training history analysis library. STHA-software is called and executed temporarily to calculate the injury risk value. In a preferable embodiment the selection of key variables minimizes the demand of resources, particularly RAM memory, and more specifically dynamic memory. The demand of resident memory is very limited, when only characteristics of each exercise are stored in RAM memory. In all embodiments there exists runtime memory with a processor and heart rate data and calculations are stored for a short time in the runtime memory during use of STHA. After an exercise only the characteristics of the executed exercise are stored in the (resident) memory, not the complete collected data. This data is stored for a longer period and remains after exercise. It is then used when the injury risk value is calculated.

The invention claimed is:

1. A method for determining injury risk of a user from plurality of exercises using a device with a heart rate sensor, a processor, memory including a resident memory, an output display device, the injury risk being determined using values depicting Short Term Training Load and Long Term Training Load, the method comprising:
   determining in each physical exercise a timestamp and a value of Short Term Training load and Long Term Training Load utilizing the heart rate sensor,
   storing the timestamp and the values of Short Term and Long Term Training load of each exercise in the resident memory obtaining a register having plurality of Short Term and Long Term values from executed exercises,
   at least one per week, automatically performing a HRV-based Recovery Test utilizing the heart rate sensor and obtaining a Recovery value with a time stamp from each Recovery Test and storing said Recovery values with the time stamp in the register of the resident memory,
   calculating indices depicting Short Term Training Load, ratio of Short Term Training Load to Long Term Training Load, and Recovery based on the values stored in the register,
   calculating weighting factors for each said index, each weighting factor depicting relevance of corresponding index to user's probability of injury,
   correcting each index with corresponding weighting factor to obtain weighted indices,
   calculating a numerical value of the Injury Risk using the weighted indices, and
   displaying the value of Injury Risk to user using the output display device.

2. The method according to claim 1, wherein said indices are calculated using scaling functions which are namely first scaling function for calculating a first index depicting Short Term Training Load, second scaling function for calculating a second index depicting ratio of Short Term Training Load to Long Term Training Load and third scaling function for calculating a third index depicting Recovery.

3. The method according to claim 2, wherein if highest value of injury risk depicts lowest possible probability of injury, the first scaling function is such that value of the first index increases to maximum as the value of Short Term Training Load increases up to a predetermined value and the value of the first index decreases as the value of Short Term Training Load increases higher than the predetermined value,
   the second scaling function is such that value of second index reduces when value of ratio of Short Term Training Load (STTL) to Long Term Training Load (LTTL) differs from 1 and the third scaling function is such that value of the third index increases when the Recovery Test result increases until a threshold value of Recovery test has been reached.

4. The method according to claim 2, wherein said third index is calculated by
   a. obtaining at least two, preferably three latest Recovery values,
   b. scaling the Recovery values using third scaling function,
   c. calculating a second average of the scaled Recovery values, the second average being the third index.

5. The method according to claim 1, the Recovery Test is a Quick Recovery Test having a duration of 1-10 minutes.

6. The method according to claim 1, the Recovery Test is a Quick Recovery Test having a duration of 2-4 minutes.

7. The method according to claim 1, wherein the values of the indices are scaled in a predetermined range in a scale 0-100.

8. The method according to claim 1, wherein said weighting factors are first weighting factor, second weighting factor and third weighting factor, wherein the first weighting factor is calculated using a first weighting function depicting reliability of the first index,
   the second weighting factor is calculated using a second weighting function depicting reliability of the second index,
   the third weighting factor is calculated using a third weighting function depicting reliability of the third index.

9. The method according to claim 8, wherein the third weighting function is an average of values of a fourth weighting function, which is a function of timing of the recovery test, and a fifth weighting function which is a function of average recovery values.

10. The method according to claim 9, wherein the third weighting factor is calculated by calculating
    a. a sub-factor for each Recovery value using the fourth weighting function and the fifth weighting function,
    b. an average of the sub-factors, the average being the third weighting factor.

11. The method according to claim 8, wherein the calculation of Injury risk comprises: multiplying the indices each with a corresponding weighting function, in which
    a. the first weighting function is constant,
    b. the second weighting function increases the value of the second weighting factor as number of exercises per week increases, c. the third weighting function gives a peak value for the third weighting factor at lowest recovery value.

12. The method according to claim 1, wherein the calculation of Injury risk comprises: scaling the values of indices stored in the register to form scaled indices wherein
  i. scaled value of the first index has a peak value before Short Term Training Load is 100% from user's personal maximum value,
  ii. scaled value of the second index has a peak value when ratio is invariable,
  iii. scaled value of the third index increases with improved recovery value until a peak value is reached,
  storing scaled indices in the register of the resident memory.

* * * * *